United States Patent
Timm

(10) Patent No.: US 6,206,924 B1
(45) Date of Patent: Mar. 27, 2001

(54) THREE-DIMENSIONAL GEOMETRIC BIO-COMPATIBLE POROUS ENGINEERED STRUCTURE FOR USE AS A BONE MASS REPLACEMENT OR FUSION AUGMENTATION DEVICE

(76) Inventor: Jens Peter Timm, 2570 San Joaquin Hills Rd., Corona Dal Mar, CA (US) 92625

( * ) Notice: Subject to any disclaimer, the term of this patent is extended or adjusted under 35 U.S.C. 154(b) by 0 days.

(21) Appl. No.: 09/421,723

(22) Filed: Oct. 20, 1999

(51) Int. Cl.[7] .................................................. A61F 2/44
(52) U.S. Cl. ..................................... 623/17.16; 623/17.11
(58) Field of Search ........................... 623/16.11, 17.16, 623/18.11, 20.16, 23.28, 23.53, 17.11; 606/60, 61, 62

(56) References Cited

U.S. PATENT DOCUMENTS

| | | | |
|---|---|---|---|
| 4,820,305 | * 4/1989 | Harms et al. | 623/16.11 |
| 4,839,215 | 6/1989 | Starling et al. . | |
| 4,863,474 | 9/1989 | Brown et al. . | |
| 5,108,435 | 4/1992 | Gustavson et al. . | |
| 5,147,402 | 9/1992 | Bohler et al. . | |
| 5,178,201 | 1/1993 | Ahlers . | |
| 5,263,986 | 11/1993 | Noiles et al. . | |
| 5,433,750 | 7/1995 | Gradinger et al. . | |
| 5,468,242 | * 11/1995 | Reisburg | 606/61 |
| 5,571,185 | 11/1996 | Schug . | |
| 5,607,424 | * 3/1997 | Tropiano | 606/61 |
| 5,609,637 | * 3/1997 | Biedermann et al. | 623/17.16 |
| 5,665,119 | 9/1997 | Koller . | |
| 5,676,700 | 10/1997 | Black et al. . | |
| 5,766,252 | * 6/1998 | Henry et al. | 623/17.16 |
| 5,897,556 | 4/1999 | Drewry et al. . | |
| 5,980,540 | * 11/1999 | Bruce | 606/60 |

* cited by examiner

Primary Examiner—Jeffrey A. Smith
Assistant Examiner—Eduardo C. Robert
(74) Attorney, Agent, or Firm—Hudak & Shunk Co.; Laura F. Shunk

(57) ABSTRACT

The invention provides a three-dimensional geometric porous engineered structure for use as a bone mass replacement or fusion augmentation device. The structure is a space-filling, self-supporting structure constructed of rigid filaments joined together to form regular, repeating geometric shapes. The structure supports the skeletal structure as well as the surrounding tissue during rehabilitation and/or bone fusion. Further, the structure provides many open intersticial areas, which are appropriately shaped and sized for bone in-growth. One preferred geometric structure is based on repeating modified dodecahedrons which are built from pentagons. The resulting structure has two transverse planes of bilateral symmetry. Other embodiments include disc shaped structures and structures having open internal areas to allow the possibility of auto graft, allograft, or artificial bone substitute.

24 Claims, 2 Drawing Sheets

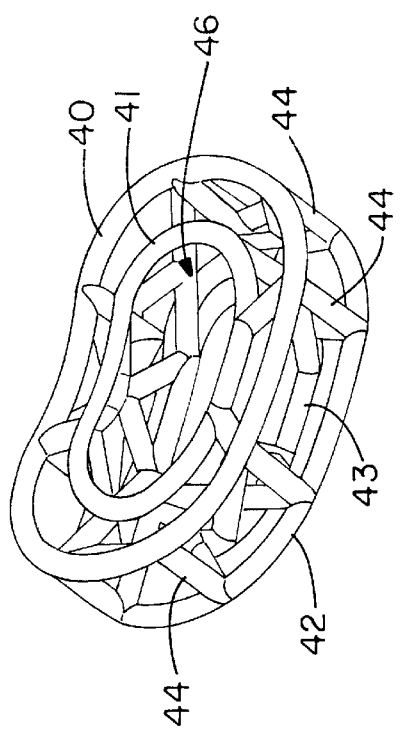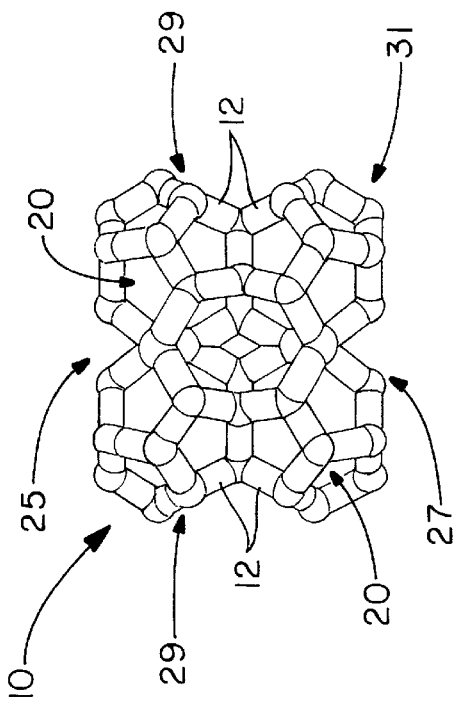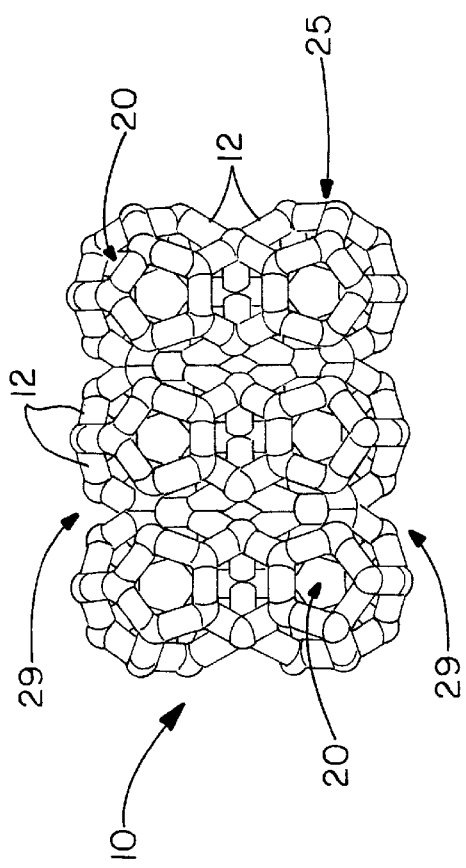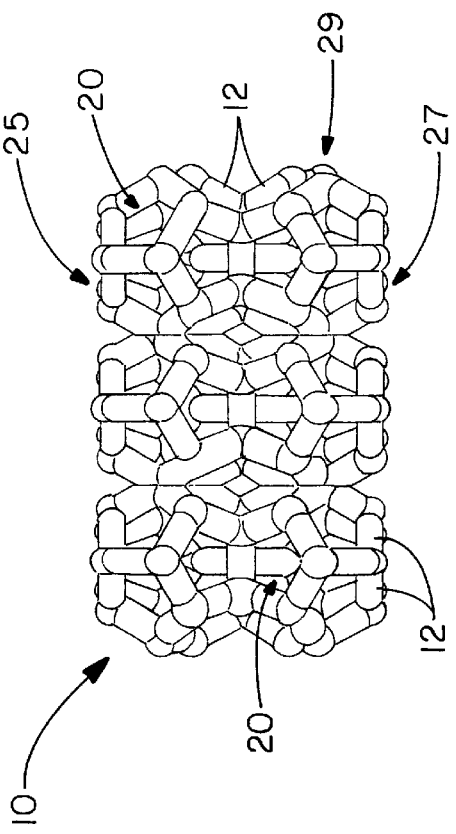

THREE-DIMENSIONAL GEOMETRIC BIO-COMPATIBLE POROUS ENGINEERED STRUCTURE FOR USE AS A BONE MASS REPLACEMENT OR FUSION AUGMENTATION DEVICE

FIELD OF THE INVENTION

The present invention relates generally to a three-dimensional structure for use as a bone mass replacement or fusion augmentation device. In particular, this structure is specifically engineered from interconnecting, non-random metallic segments so as to minimize the volume of the metal to void and thereby maximize potential volume for reconstructive bone growth. The metallic segments or filaments are joined to form regular repeating geometric shapes to provide maximum strength and minimize potential shear planes through the structure. A particularly favored geometric shape is a modified dodecahedron based on pentagons. The resulting structure may have a general rectangular block configuration, a cylindrical configuration which can include a larger defined void area in the center.

SUMMARY OF THE INVENTION

The present invention provides an engineered three-dimensional structure, which has a goal of providing a structure for bone to grow through for fusion or reconstructive surgery. The structure is further intended to be strong enough to provide support to the skeletal and muscular structure during bone rehabilitation, i.e. during the healing process when bone reconstruction occurs.

Thus, it is a goal of the present invention to provide a structure which is self-supporting meaning that no further substrate or support is required to provide the necessary support characteristics during rehabilitation. This contrast with implants such as acetabular cups having porous coatings. Likewise, these coatings can also be distinguished since the pores tend to be random and substantially distinguished since the pores tend to be random and substantially smaller (by at least a magnitude or more of size) than the pores of the present invention.

Further, the structure is constructed of discrete subcomponents which are repeating geometric shapes, constructed of filamentary elements so as to provide regular intersticial pores and/or voids of an appropriate shape and size to allow for bone. Thus, while the filamentary segments are providing structural support, slow in-growth can occur into the void area. This growth, can be encouraged and/or augmented through the use of bone graft or bone substitutes. By "regular" it is meant that the component parts are uniform, or of the same kind or structure or shape or size, or having repeating units of the same size and/or angle. By "geometric" it is meant that at least some of the component parts are formed of straight lines, bars, or crosses. By "ordered" it is meant that the shapes are arranged in a sequence or pattern which is not random but which possesses symmetry and/or repetition. In a further embodiment the structure has a central void area to accommodate the bone graft or bone substitute.

An additional aspect of the invention is the provision of a structure, which is "space-filling" meaning that structure can be expanded to any size and will maintain its shape as a repeating structure. Thus, the structure is ordered and not random. It is homogeneous and provides multiple planes of symmetry.

The implant is preferably constructed from a bio-compatible cast metal such as titanium or a titanium alloy so as to maximize strength and minimize the metal artifact which would appear on sectional CT scans. The structure can be modified to generate the desired implant stiffness for a variety of applications. The structure can also be modified to increase its strength and resistance to fatigue as is necessary. Further, once the fundamental structure has been established by constructing the component repeating shapes, individual filamentary members may be modified or eliminated to provide for functional structures including for example voids for bone growth voids or means to attach fasteners.

Potential applications include spinal fusions such as posterior lumbar inter-body fusion ("PLIF"), anterior lumbar and inter-body fusion ("ALIF"), inter-body fusion ring, long-bone reconstruction such as humoral or femoral reconstruction, tibial-plateau reconstruction, cranial facial applications including mixillo-facial reconstruction, and pelvic-defect reconstruction. Thus, in general, the present structure has many orthopaedic applications for reinforcing weak, bony tissue.

BRIEF DESCRIPTION OF THE DRAWINGS

FIG. 1 shows a side view of first embodiment of the invention;

FIG. 2 shows an end view of first embodiment shown in FIG. 1;

FIG. 3 shows a top view of the embodiment shown in FIG. 1;

FIG. 4 shows a second embodiment of the invention for use in anterior lumbar inner-body fusion;

DESCRIPTION OF THE INVENTION

Figure 5:
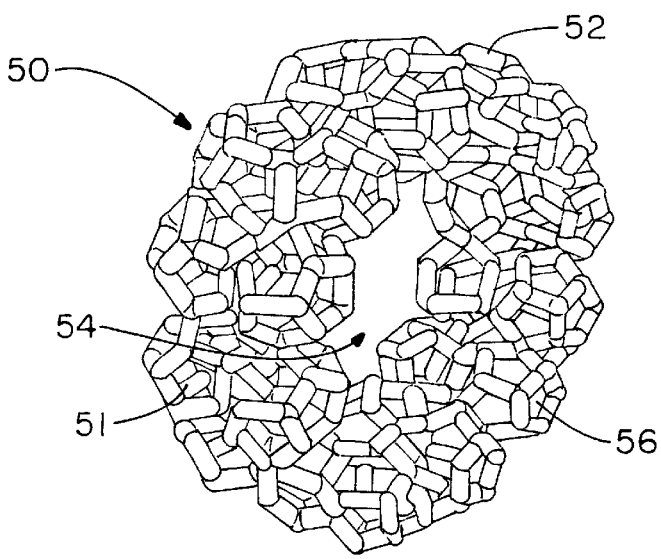
FIG. 5 shows a third, annular, embodiment of the invention.

FIG. 1 illustrates a three-dimensional, geometric-porous engineered structure for use as a bone mass replacement for fusion augmentation device. The structure, shown generally at 10 is formed from a series of inter-connected filaments 12, which form one or more types of repeating geometric shapes. In the structure shown in FIGS. 1–3, a first shape 15 is pentagonal, while a second repeating shape is a modified dodecahedron 17. The shapes interconnect so as to define porous areas of intersticial voids 20. These areas provide space for bone to grow into during bone reconstruction or fusion. Thus, the structure is intended ultimately to become redundant and/or subplanted by the bone that grows into the area.

As can be seen in particular in FIGS. 1–3, the structure 10 has a generally regular overall shape. In this instance, the structure has a block configuration with the top 25, bottom 27, side 29 and end 31 geometric structures substantially defining planes. However, as is also evident, the structure is generally lacking "shear planes", i.e. planes predisposed to shear failure within the structure. This aspect of the invention allows for the maximization of strength in every direction, including characteristics for axial, shear, and torsional stresses 10 to which bones are subjected, while minimizing the metallic, scaffolding or substructure.

FIG. 4 illustrates an embodiment of the invention for use in spinal inter-body fusion. In particular, this disc or kidney-shaped device has inner 41 an outer 40 top rings and inner 43 and outer 42 bottom rings inter-connected by filamentary struts 44 to provide the desired strength characteristics. Further, this device has a larger void 46 defined by interior rings to allow bone graft, or bone substitute to be implanted within the structure.

A similar ring implant for reinforcing weak, bony tissue is shown at 50 in FIG. 5. This structure is illustrated as having filamentary pentagons constructed of individual filaments 52 defining pores 51 and dodecahedron shapes similar to those shown in the first embodiment shown in FIGS. 1–3. However, similar to the embodiment shown in FIG. 4, the implant in FIG. 5 is ring shaped and thus includes an interior void 54 intended for the same purpose as in FIG. 4.

Figure 6:
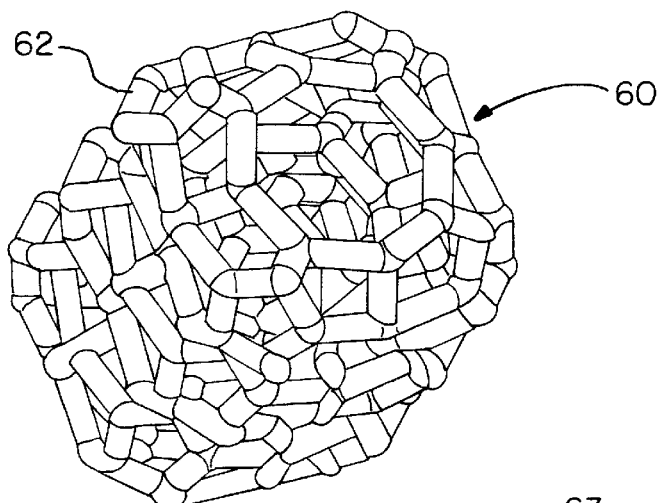
FIG. 6 shows a view of a fourth embodiment.
Figure 7:
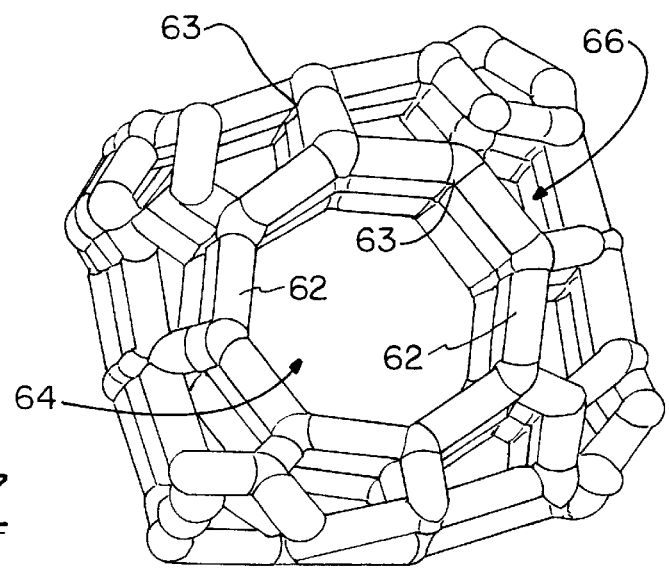
FIG. 7 shows a different view and scale of the embodiment of FIG. 6.

FIGS. 6 and 7 illustrate a block-shaped structure 60 again constructed from filaments 62 joined at regular repeating angles 63 to form modified pentagons and highly modified dodecahedrons. By "modified" is meant that one or more angles of the basic shape or one or more filamentary segment length has been modified from the general understanding of this geometric shape to allow the figure to close and to connect the pieces of the three-dimensional space-filling structure. A pentagon is a regular five-sided shape while a dodecahedron is a spherical structure formed by joining ten pentagons. This structure also has a central void 64 defined by closed octagonal inner rings 66.

Characteristics which may be considered in the design of specific structures for a particular application include compression, shear rotations and torsion as tested in accordance with ASTM draft of medical testing. The filaments generally have a thickness of from about 0.25 millimeters to 2 millimeters preferably 0.5 to 1.5 millimeters and most preferably 0.5 to 1 millimeter. The length of these filaments in a pentagonal shape is generally from about 1 millimeter to about 10 millimeters and, preferably 1 to 6 millimeters and most preferably 1.5 to 3 millimeters. The dodecahedron shape has a maximum size of 20 millimeters. While cast titanium or titanium alloy are envisioned as a preferable material, the invention could be made of other biocompatible substances including for example, PEEK, other metals, and ceramic bone substitutes could also be envisioned.

In general, the geometry used for the present invention envisions regular repeating convex polyhedra in three-dimensional space including for example the tetrahedron, the cube, the regular octahedron, the pentagonal dodecahedron bounded by 12 regular pentagons and the icosahedron, bounded by 20 regular triangles. Thus, the filamentary structures are joined together to form geometric shapes, which are the building blocks to form a larger configuration, meaning the general overall profile of the structure. Thus, the present invention would envision other configurations or structures based on these kinds of geometric shapes as well.

While in accordance with the patent statutes the best mode and preferred embodiment have been set forth, the scope of the invention is not limited thereto, but rather by the scope of the attached claims.

What is claimed is:

1. A self-supporting bio-compatible porous three dimensional structure for skeletal rehabilitation comprising;
   inter-connected rigid filaments collectively defining a series of at least two repeating ordered open 3-dimensional shapes.

2. A self-supporting porous three-dimensional structure a set forth in claim 1, wherein said filaments are connected so as to define repeating geometric shapes.

3. A self-supporting porous three-dimensional structure a set forth in claim 2, wherein at least one of said repeating shapes are five-sided.

4. A self-supporting porous three-dimensional structure a set forth in claim 3, wherein at least one of said repeating shapes is a pentagon.

5. A self-supporting porous three-dimensional structure a set forth in claim 2, wherein at least one of said repeating shapes is 10 sided.

6. A self-supporting porous three-dimensional structure a set forth in claim 5, wherein said shape is a modified dodecahedron.

7. A self-supporting porous three-dimensional structure a set forth in claim 1, wherein the filament is metal.

8. A self-supporting porous three-dimensional structure a set forth in claim 7, wherein the filament is titanium.

9. A self-supporting porous three-dimensional structure a set forth in claim 8, wherein said structure is a bone implant.

10. A self-supporting porous three-dimensional structure a set forth in claim 9, wherein said structure is a three-dimensional, self-supporting, space-filling structure having interconnected solid elements together defining repeating open structures and having no shear planes.

11. An orthopedic implant comprising;
    a structure having sides, each side comprising non-random inter-connected 3-dimensionally oriented bio-compatible filaments which define pores, said structure being substantially free from planes predisposed to shear failure.

12. An orthopedic implant as set forth in claim 11 further comprising a void internal to said structure for bone graft or bone substitute.

13. An orthopedic implant as set forth in claim 11, wherein said structure has a top which defines a substantially planar first surface and a bottom, which defines a substantially planar surface substantially parallel to said first surface.

14. An orthopedic implant as set forth in claim 13, wherein said filaments are connected so as to define repeating geometric shapes.

15. An orthopedic implant as set forth in claim 14, wherein at least one of said repeating shapes are five-sided.

16. An orthopedic implant as set forth in claim 15, wherein at least one of said repeating shapes is a pentagon.

17. An orthopedic implant as set forth in claim 16, wherein at least one of said repeating shape is 10 sided.

18. An orthopedic implant as set forth in claim 17, wherein said shape is a modified dodecahedron.

19. An orthopedic implant as set forth in claim 11, wherein the filament is metal.

20. An orthopedic implant as set forth in claim 19, wherein the filament is titanium.

21. An orthopedic implant comprising a structure having a central opening surrounded by at least one mesh wall having pores oriented in three dimensions and comprising bio-compatible, metallic filaments which are interconnected to form discrete sub-components which comprise a repeating pattern of geometric shapes that define said pores.

22. An orthopedic implant as set forth in claim 21 wherein said filaments are connected to form at least two basic repeating geometric configurations.

23. An orthopedic implant as set forth in claim 22 wherein said filaments define multiple planes of symmetry.

24. An orthopedic implant as set forth in claim 23 wherein said filaments are titanium.

\* \* \* \* \*

UNITED STATES PATENT AND TRADEMARK OFFICE
CERTIFICATE OF CORRECTION

PATENT NO.   : 6,206,924 B1
DATED        : March 27, 2001
INVENTOR(S)  : Jens Peter Timm It is certified that error appears in the above-identified patent and that said Letters Patent is hereby corrected as shown below:

<u>Title page,</u>
Item [73], Assignee was omitted. Please add -- Assignee: Interpore Cross International, 181 Technology Drive, Irvine, CA 92618 --

Signed and Sealed this

Fifteenth Day of January, 2002

Attest:

JAMES E. ROGAN
*Director of the United States Patent and Trademark Office*

*Attesting Officer*